US009707318B2

(12) United States Patent
Mousa et al.

(10) Patent No.: US 9,707,318 B2
(45) Date of Patent: Jul. 18, 2017

(54) COMPOSITIONS OF NOVEL BONE PATCH IN BONE AND VASCULAR REGENERATION

(76) Inventors: Shaker A. Mousa, Wynantskill, NY (US); Mohammed H. Qari, Jeddah (SA); Mohammed S. Ardawi, Jeddah (SA)

( * ) Notice: Subject to any disclaimer, the term of this patent is extended or adjusted under 35 U.S.C. 154(b) by 633 days.

(21) Appl. No.: 12/912,853

(22) Filed: Oct. 27, 2010

(65) Prior Publication Data
US 2011/0104230 A1 May 5, 2011

Related U.S. Application Data

(60) Provisional application No. 61/279,963, filed on Oct. 29, 2009.

(51) Int. Cl.
*A61F 2/00* (2006.01)
*A01N 63/00* (2006.01)
*A61L 27/38* (2006.01)
*A61L 27/10* (2006.01)
*A61L 27/20* (2006.01)
*A61F 2/28* (2006.01)

(52) U.S. Cl.
CPC ........... *A61L 27/3821* (2013.01); *A61L 27/10* (2013.01); *A61L 27/20* (2013.01); *A61F 2/2846* (2013.01); *A61F 2002/2817* (2013.01); *A61L 2430/02* (2013.01)

(58) Field of Classification Search
CPC ........ A61L 27/243; A61L 27/20; A61L 27/10; A61L 27/3821
USPC ......................................................... 424/423
See application file for complete search history.

(56) References Cited

U.S. PATENT DOCUMENTS

| | | | |
|---|---|---|---|
| 3,224,942 A | 12/1965 | Martin | |
| 6,541,024 B1 * | 4/2003 | Kadiyala et al. | 424/426 |
| 7,897,588 B2 * | 3/2011 | Parhami | 514/182 |
| 8,178,013 B2 * | 5/2012 | Kim | 264/40.5 |
| 2005/0053668 A1 | 3/2005 | Vail | |
| 2005/0220773 A1 * | 10/2005 | Uemura et al. | 424/93.21 |
| 2007/0053987 A1 | 3/2007 | Bayer et al. | |
| 2007/0237827 A1 | 10/2007 | Sung et al. | |
| 2009/0087431 A1 * | 4/2009 | Yaworsky et al. | 424/133.1 |

FOREIGN PATENT DOCUMENTS

JP 11012192 1/1999

OTHER PUBLICATIONS

Yamada et al., 2003, J. Cranio-Maxillofacial Surgery 37: 27-33.*
Leach et al., 2004, Exp. Opin. Biol. Ther. 4:1015-1027.*
Reyes et al., 2002, J. Clin. Invest. 109:337-346.*
Zhou et al., Aug. 2009; Exp. Cell. Res 315:2953-2962.*
Schofer et al., Apr. 2009, The Scientific World J. 9:313-319.*
Abdallah et al., Aug. 2008, J. Cell. Physiol 218:9-12.*
Gang et al 2006, Cytotherapy 8:215-227.*
Yamada et al 2003, J. Cranio-Maxillofacial Surgery 31:27-33.*
Boo et al (2002, J. Craniofacilal. Surg. 13:231.*
Yan et al 2007, Zhongguo Xiu Fu Chong Jian Wai Ke Za Zhi 21;76-80; Abstract p. 1 of 1.*
Zhou et al Aug. 2009; Exp. Cell. Res. 315:2953-2962.*
Arthur et al., 2009:, J. Cell. Physiol. 218:237-245.*
Ray et al 2008, Mol. Med 14:493-501.*
Erwin et al (2009, J. Surgical Research 152:319-324.*
Oswald et al 2004, Stem Cells 22:377-384.*
Backesjo et al 2006, J. Bone and Mineral Res. 21:993-1002.*
Rasbach et al 2008 J. Pharmacol. Exp. Therap. 325:536-543.*
Elabd et al (2008, Stem Cells 26:2399-2407; Abstract p. 1.*
Whitney & Rolfes, Understanding Nutrition. Ninth edition, 2002, Wadsworth Group; Vitamin D, Chapter 11; pp. 363-368.
Assessment of Fracture Risk and Its Application to Screening for Postmenopausal Osteoporosis; Report of a WHO Study Group. World Health Organization Technical Report Series, Geneva 1994; 843; pp. 1-129.
Mayes, Stacey, L.; Review of Postmenopausal Osteoporosis Pharmacotherapy; Nutrition in Clinical Practice; Jun. 2007: 22; pp. 276-285.
Who Are Candidates for Prevention and Treatment for Osteoporosis? Osteoporosis International (1997) 7; pp. 1-6.
Cashman, Kevin D.; Diet, Nutrition and Bone Health. The Journal of Nutrition; Nov. 2007; 137, 11S; Research Library; Supplement; pp. 2507S-2512S.
National Osteoporosis Foundation. America's Bone Health: The State of Osteoporosis and Low Bone Mass in Our Nation; Washington DC: National Osteoporosis Foundation; 2002. G-830; 16 pages.
Cooper et al.; Population-Based Study of Survival after Osteoporotic Fractures; American Journal of Epidemiology; 1993; vol. 137, No. 9; pp. 1001-1005.
Leibson et al.; Mortality, Disability, and Nursing Home Use for Persons with and without Hip Fracture: A Population-Based Study; 2002 by the American Geriatrics Society; JAGS 50; pp. 1644-1650.
Magaziner et al.; Excess Mortality Attributable to Hip Fracture in White Women Aged 70 Years and Older; American Journal of Public Health, Oct. 1997, vol. 87, No. 10; pp. 1630-1636.
Magaziner et al.; Predictors of Functional Recovery One Year Following Hospital Discharge for Hip Fracture: A Prospective Study; Journal of Gerontology:Medical Sciences, May 1990, vol. 45, No. 3; pp. M101-M107.
Magaziner et al.; Excess Mortality Attributable to Hip Fracture in White Women Aged 70 Years and Older; American Journal of Public Health, Oct. 1997, vol. 87, No. 10; pp. 1630-1636.
Magaziner et al.; Predictors of Functional Recovery One Year Following Hospital Discharge for Hip Fracture: A Prospective Study; Journal of Gerontology:Medical Sciences, May 1990, vol. 45, No. 3; pp. M101-M107.

(Continued)

*Primary Examiner* — Christopher M Babic
*Assistant Examiner* — Kelaginamane T Hiriyanna
(74) *Attorney, Agent, or Firm* — Schmeiser, Olsen & Watts, LLP

(57) ABSTRACT

A bone patch and method for treating a bone condition of an animal. The bone patch includes a composition of ingredients. The composition of ingredients include: stem cells; signaling molecules for osteoblast/endothelial differentiation; and scaffold material. The method for treating a bone condition includes: applying the bone patch to the animal for bone regeneration, treatment of a fractured bone, and/or treatment of a bone disorder.

7 Claims, 1 Drawing Sheet

(56) References Cited

OTHER PUBLICATIONS

Riggs et al.; The Worldwide Problem of Osteoporosis: Insights Afforded by Epidemiology; Bone, vol. 17, No. 5 Supplement; Nov. 1995; pp. 505S-511S.
Kannus et al.; Epidemiology of Osteoporotic Ankle Fractures in Elderly Persons in Finland; Dec. 15, 1996 Annals of Internal Medicine; vol. 125, No. 12; pp. 975-978.
Gullberg et al.; World-wide Projections for Hip Fracture; Osteoporos Int (1997) 7; pp. 407-413.
Cooper et al.; Hip Fractures in the Elderly: A World-Wide Projection; Osteoporos Int (1992), 2; pp. 285-289.
Ahmadi-Abhari et al.; Burden of Hip Fracture in Iran; Calcified Tissue International (2007) 80; pp. 147-153.
Lau, Edith M. C.; Epidemiology of Osteoporosis; Best Practice & Research Clinical Rheumatology (2001), vol. 15, No. 3; pp. 335-344.
Osteoporosis Society of India (Feb. 10, 2003) Action Plan Osteoporosis; Consensus statement of an expert group; New Delhi; pp. 1-34.
Shatrugna et al.; Bone status of Indian women from a low-income group and its relationship to the nutritional status. Osteoporos Int (2005) 16; pp. 1827-1835.
Rowe et al.; An Epidemiological Study of Hip Fracture—A Comparison Between 1991 and 2001. Korean Journal of Bone Metabolism (2003) 10; pp. 109-120.
Ghannam et al.; Bone Mineral Density of the Spine and Femur in Healthy Saudi Females: Relation to Vitamin D Status, Pregnancy, and Lactation; Calcified Tissue International (Jul. 1999) 65; pp. 23-28.
Bubshait et al.; Economic Implications of Osteoporosis-Related Femoral Fractures in Saudi Arabian Society; Calcified Tissue International (2007) 81; pp. 455-458.
Sadat-Ali et al.; Effect of parity on bone mineral density among postmenopausal Saudi Arabian women; Saudi Med J 2005; vol. 26 (10); pp. 1588-1590.
El-Desouki, Mahmoud; Bone Mineral Density of the Spine and Femur in the Normal Saudi Population; Saudi Medical Journal 1995; 16(1): pp. 30-35.
Sadat-Ali et al.; Osteoporosis among male Saudi Arabs: a pilot study; Ann Saudi Med 26(6) Nov.-Dec. 2006; pp. 450-454.
El-Desouki et al.; High prevalence of osteoporosis in Saudi men; Saudi Medical Journal 2007; vol. 28, No. 5; pp. 774-777.
International Osteoporosis Foundation, Facts and statistics about osteoporosis and its impact. [online]. 9 pages. [retrieved on May 5, 2008]. Retrieved from the Internet: < URL: http://www.iofbonehealth.org/facts-and-statistics.html>.
Akkas et al.; Effect of Medication on Biomechanical Properties of Rabbit Bones: Heparin Induced Osteoporosis; Clinical Rheumatology, 1997, vol. 16, No. 6; pp. 585-595.
Bellingham et al.; Bisphosphonate (Pamidronate/APD) Prevents Arthritis-Induced Loss of Fracture Toughness in the Rabbit Femoral Diaphysis; Journal of Orthopaedic Research (1995); vol. 13, No. 6; pp. 876-880.
Huang et al.; Osteoblastic Differentiation of Rabbit Mesenchymal Stem Cells Loaded in a Carrier System of Pluronic F127 and Interpore; Chang Gung Med J. vol. 29, No. 4 Jul.-Aug. 2006; pp. 363-372.
Ketchen et al.; The biological effects of magnetic fields on man; American Industrial Hygiene Association Journal 1978 (39); pp. 1-11.
Cook et al.; The Otto Aufranc Award; Strut Allograft Healing to the Femur—With Recombinant Human Osteogenic Protein-1; Clinical Orthopaedics and Related Research 2000, No. 381; pp. 47-57.
Ripamonti, U.; Bone induction by recombinant human osteogenic protein-1 (hOP-1, BMP-7) in the primate Papio ursinus with expression of mRNA of gene products of the TGF-beta superfamily; Journal of Cellular and Molecular Medicine, 2005, vol. 9, No. 4; pp. 911-928.
Deibert et al.; Ion Resonance Electromagnetic Field Stimulation of Fracture Healing in Rabbits with a Fibular Osteotomy; Journal of Orthopaedic Research (1994) vol. 12, No. 6; pp. 878-885.
Bruce et al.; Effect of a Static Magnetic Field on Fracture Healing in a Rabbit Radius; Preliminary Results; Clinical Orthopaedics and Related Research, Sep. 1987; No. 222: pp. 300-305.
Bharali et al.; Cross-linked polyvinylpyrrolidone nanoparticles: a potential carrier for hydrophilic drugs; Journal of Colloid and Interface Science 258 (2003); pp. 415-423.
Kumar et al.; Efficacy of Lytic Peptide-Bound Magnetite Nanoparticles in Destroying Breast Cancer Cells; Journal of Nanoscience and Nanotechnology 2004, vol. 4, No. 3; pp. 245-249.
U.S. Appl. No. 12/912,826, filed Oct. 27, 2010, Confirmation No. 2783.
U.S. Appl. No. 12/912,902, filed Oct. 27, 2010, Confirmation No. 2889.
Abdullah bin Habeeballah bin Abdullah Juma, "The Effects of Lepidium sativum Seeds on Fracture-Induced Healing in Rabbits", MedGenMed. 2007; 9(2): 23 (13 pages).
S. K. Ahsan, M. Ta Riq, M. Ageel, M. A. Alyahyaand A. H. Shah, "Studies on Some Herbal Drugs Used in Fracture Healing", International Journal of Crude Drug Research, 27 (1989), No. 4, pp. 235-239.
Sheel Sharma and Nidhi Agarwal, "Nourishing and healing prowess of garden cress (*Lepidium sativum* Linn.)—A review", Indian Journal of Natural Products and Resources, 2(3), 2011, 292-297.
S.O. Bafeel and S.S. Ali, "The Potential Liver Toxicity of Lepidium sativum Seeds in Albino Rats", Research Journal of Biological Sciences, 4(12): 1250-1258, 2009.
Lingjie Fu, Tingting Tang, Yanying Miao, Yongqiang Hao and Kerong Dai, "Effect of 1 ,25-dihydroxy vitamin D3 on fracture healing and bone remodeling in ovariectomized rat femora", Bone 44 (2009) 893-898.
Peter F. Brumbaugh, Donald P. Speer and Michael J. Pitt, "A Metabolite of Vitamin D That Promotes Bone Repair", American Journal of Pathology, 1982, 106:171-179.
Sha Jin and Kaiming Ye, "Nanoparticle-Mediated Drug Delivery and Gene Therapy", Biotechnology Progress 2007, 23, 32-41.
Chen-Guang Liu, Kashappa Goud H. Desai, Xi-Guang Chen and Hyun-Jin Park, "Linolenic Acid-Modified Chitosan for Formation of Self-Assembled Nanoparticles", Journal of Agricultural and Food Chemistry 2005, 53, 437-441.
T. P. Dew, A. J. Day and M. R. A. Morgan, "Bone mineral density, polyphenols and caffeine: a reassessment", Nutrition Research Reviews (2007), 20, 89-1 05.
Sophie E. Putnam, Andy M. Scutt, Katrina Bicknell, Caroline M. Priestley and Elizabeth M. Williamson, "Natural Products as Alternative Treatments for Metabolic Bone Disorders and for Maintenance of Bone Health", Phytotherapy Research 21, 99-112 (2007).
M. Prabaharan and J. F. Mano, "Chitosan-Based Particles as Controlled Drug Delivery Systems", Drug Delivery, 12:41-57, 2005.
Mehrdad Hamidi, Amir Azadi and Pedram Rafiei, "Hydrogel nanoparticles in drug delivery", Advanced Drug Delivery Reviews 60 (2008) 1638-1649.
Beom-Su Kim, Cheoi-Sang Kim and Kang-Min Lee, "The Intracellular Uptake Ability of Chitosan-coated Poly (D,L-lactidecoglycolide) Nanoparticles", Archives of Pharmaceutical Research vol. 31, No. 8, 1050-1054, 2008.
N Nafee, S Taetz, M Schneider, UF Schaefer, C-M Lehr. "Chitosan-coated PLGA nanoparticles for DNA/RNA delivery: effect of the formulation parameters on complexation and transfection of antisense oligonucleotides." Nanomedicine: Nanotechnology, Biology, and Medicine. vol. 3, 2007, pp. 173-183.
Final Office Action (Mail Date Oct. 31, 2012) for U.S. Appl. No. 12/912,902; filed Oct. 27, 2010; Confirmation No. 2889.
Office Action (Mail Date Sep. 7, 2012) for U.S. Appl. No. 12/912,826; filed Oct. 27, 2010; Confirmation No. 2783.

\* cited by examiner

COMPOSITIONS OF NOVEL BONE PATCH IN BONE AND VASCULAR REGENERATION

CROSS-REFERENCES TO RELATED APPLICATIONS

This patent application claims priority to U.S. Provisional No. 61/279,963, filed on Oct. 29, 2009, which is incorporated herein by reference in its entirety.

FIELD OF THE INVENTION

This invention pertains to methods and compositions for bone patch for bone regeneration, treatment of a fractured bone, and/or treatment of a bone disorder.

BACKGROUND OF THE INVENTION

Osteoporosis, which literally means "porous bone", leads to literally abnormally porous bone that is more compressible like a sponge, than dense like a brick. Osteoporosis is a disease with a very wide distribution all over the world. Osteoporosis leads to bones being porous and fragile, and the complications of this disease include fractures and delayed healing. The burdens of such global problem are immense to the health care providers due to the increasing cost of treatment and prevention, and the increasing morbidity and mortality. Although neither calcium nor vitamin D has been shown to prevent osteoporosis in postmenopausal women alone, the combination does. Both calcium and vitamin D are commonly used in the treatment of osteoporosis. The estrogens and raloxifene both prevent bone loss in postmenopausal women, and the estrogens probably also decrease the risk of first fracture. There is good evidence that raloxifene prevents further fractures in postmenopausal women who have already had fractures and some evidence that estrogen does as well. Calcitonin increases bone mineral density in early postmenopausal women and men with idiopathic osteoporosis, and also reduces the risk of new fractures in osteoporotic women. The bisphosphonate alendronate prevents bone loss and reduces fractures in healthy and osteoporotic postmenopausal women, and in osteoporotic men. Risedronate is more potent and has fewer upper gastrointestinal side effects than alendronate, and reduces the incidence of fractures in osteoporotic women. Intermittent use of the potent bisphosphonate zoledronate also increases bone mineral density and may become an alternative in the prevention and treatment of osteoporosis. All of the agents discussed above prevent bone resorption, whereas teriparatide increases bone formation and is effective in the treatment of osteoporotic women and men. In the treatment of secondary osteoporosis associated with the use of glucocorticoids to treat inflammation or prevent rejection after transplantation, the bisphosphonates are effective. The agents that have undergone some clinical trialing as new or alternative drugs for the treatment of osteoporosis include tibolone, new SERMs, androgens, growth hormone, insulin-like growth factor-1 and stontium ranelate. The targets/drugs that are being developed to inhibit bone resorption include the OPG/RANKL/RANK system, cathepsin K inhibitors, vitronectin avb3 receptor antagonists, estren, the interleukin-6 and gp130 system, cytokines and growth factors. New drugs/targets to promote bone formation include the commonly used lipid-lowering statins and the calcilytic release of parathyroid hormone (PTH).

Many international and local studies are published including those from Saudi Arabia and Arabian gulf states all agrees on the increasing risks of osteoporosis. Fractures and its complications, and the need to have more emphasis on research that leads to improvement of the strategies of prevention and treatment.

Osteoporosis is a disease in which bones become fragile and more likely to break on minimal trauma. Osteoporosis is a condition of older persons (Whitney & Rolfes, Understanding Nutrition, Ninth edition, 2002, Wadsworth Group). A World Health Organization (WHO) has defined osteoporosis as "A disease characterized by low bone mass and micro-architectural deterioration of bone tissue, leading to enhanced bone fragility and a consequent increase in fracture risk" (Assessment of fracture risk and its application to screening for postmenopausal osteoporosis, Report of a WHO Study Group, World Health Organ Tech Rep Ser 1994; 843:1-129). According to this definition, the diagnosis of osteoporosis requires the presence of a fracture risk. The World Health Organization now defines osteoporosis by bone mineral density (BMD) measurement, which allows diagnosis and treatment of osteoporosis prior to incident fracture. The major complication of osteoporosis is an increase in fragility fractures leading to morbidity, mortality, and decreased quality of life. The osteoporosis process can operate silently for decades. Osteoporosis is known as the silent thief because the bone loss occurs without symptoms.

Osteoporosis is an important public health issue: Osteoporosis is a major public health threat for an estimated 44 million Americans or 55 percent of the people 50 years of age and older. Of these over 10 million people have been diagnosed as having osteoporosis (Mayes. Review of post menopausal osteoporosis pharmacology. Nutr. Clin. Prac. 2007: 22; 276 to 285). 12.5% of all Europeans over the age of 50 are likely to receive a spinal fracture of some kind in any given year. An estimated 75 million people in Europe, the United States, and Japan have osteoporosis (Who are candidates for prevention and treatment for osteoporosis?).

In the U.S. today, almost 34 million more are estimated to have low bone mass, placing them at increased risk for osteoporosis (Cashman (2007), Diet, Nutrition and Bone Health. Journal of Nutrition, Supplement: 2507S to 2512S). According to the World Health Organization, 55% of the people over the age of 50 years in the USA suffer from osteoporosis (National Osteoporosis Foundation, America's Bone Health: The State of Osteoporosis and Low Bone Mass in Our Nation, Washington D.C.: National Osteoporosis Foundation; 2002).

Hip fractures cause the most morbidity with reported mortality rates up to 20-24% in the first year after a hip fracture (Cooper C, Atkinson E J, Jacobsen S J, et al. (1993), Population-based study of survival after osteoporotic fractures, Am J Epidemiol 137:1001; Leibson C L, Tosteson A N, Gabriel S E, et al. (2002), Mortality, disability, and nursing home use for persons with and without hip fracture: a population-based study, J Am Geriatr Soc 50:1644.), and greater risk of dying may persist for at least 5 years afterwards (Magaziner J, Lydick E, Hawkes W, et al. (1997), Excess mortality attributable to hip fracture in white women aged 70 years and older, Am J Public Health 87:1630). Loss of function and independence among survivors is profound, with 40% unable to walk independently, 60% requiring assistance a year later (Magaziner J, Simonsick E M, Kashner T M, et al. (1990), Predictors of functional recovery one year following hospital discharge for hip fracture: a prospective study, J Gerontol 45:M101). Because of these losses, 33% are totally dependent or in a nursing home in the year following a hip fracture (Cooper C, Atkinson E J, Jacobsen S J, et al. (1993), Population-based study of survival after osteoporotic fractures, Am J Epidemiol 137: 1001; Riggs B L and Melton L J, 3rd (1995), The worldwide problem of osteoporosis: insights afforded by epidemiology, Bone 17:505 S; Kannus P, Parkkari J, Niemi S and Palvanen M (1996), Epidemiology of osteoporotic ankle fractures in elderly persons in Finland. Ann Intern Med 125:975).

In Asia it is projected that more than about 50% of all osteoporotic hip fractures will occur in Asia by the year 2050 (Gullberg B, Johnell O and Kanis J A (1997), World-wide projections for hip fracture, Osteoporos Int 7:407. & Cooper C, Campion G and Melton L J, 3rd (1992), Hip fractures in the elderly: a world-wide projection. Osteoporos Int 2:285).

Iran accounts for 0.85% of the global burden of hip fracture and 12.4% of the burden of hip fracture in the Middle East (madi-Abhari S, Moayyeri A and Abolhassani F (2007), Burden of hip fracture in Iran. Calcif Tissue Int 80:147). In Hong Kong in 1996, the acute hospital care cost of hip fracture per year amounted to $17 million (Lau E M (2001), Epidemiology of osteoporosis, Best Pract Res Clin Rheumatol 15:335). For India, expert groups peg the number of osteoporosis patients at approximately 26 million (2003 figures) with the numbers projected to increase to 36 million by 2013 (Osteoporosis Society of India (2003), Action Plan Osteoporosis: Consensus statement of an expert group, New Delhi). In a study among Indian women aged 30-60 years from low income groups, BMD at all the skeletal sites were much lower than values reported from developed countries, with a high prevalence of osteopenia (52%) and osteoporosis (29%) thought to be due to inadequate nutrition (Shatrugna V, Kulkarni B, Kumar P A, et al. (2005), Bone status of Indian women from a low-income group and its relationship to the nutritional status, Osteoporos Int 16:1827). In Japan, new hip fractures increased a dramatic 1.7-fold in the 10 years from 1987 to 1997 (Rowe S M (2003), An epidemiological study of hip fracture: a comparison between 1991 and 2001, Korean J Bone Metab 10:109). In Korea, the occurrence of hip fractures increased about 4-fold over 10 years (1991-2001) (Rowe S M (2003), An epidemiological study of hip fracture: a comparison between 1991 and 2001, Korean J Bone Metab 10:109).

In Saudi Arabia in 52% of examined Saudi Arabian females for example, vitamin D level was extremely low (because of clothes that block almost all sunlight), but their bones were not affected (Ghannam N N, et al, Bone mineral density of the spine and femur in healthy Saudi females: relation to vitamin D status, pregnancy, and lactation, Calcif Tissue Int 1999 July; 65(1):23-8). In Saudi Arabia with a population of 1,461,401 persons aged 50 years or more, 8,768 would suffer femoral fractures yearly at a cost of $1.14 billion (Bubshait D and Sadat-Ali M (2007), Economic implications of osteoporosis-related femoral fractures in Saudi Arabian society. Calcif Tissue Int 81:455). A study that was conducted in the eastern region of Saudi Arabia concluded that the incidence of PMO in Saudi Arabian women is reportedly higher in comparison to women in Western countries (Sadat-Ali M, Al-Habdan I, Al-Mulhim F A, El-Hassan A Y, Effect of parity on bone mineral density among postmenopausal Saudi Arabian women, Saudi Med J 2005; 26: 1588-90; El-Desouki M. Bone mineral density of the spine and femur in the normal Saudi population, Saudi Med J 1995; 16: 30-35). Another report in the eastern region of Saudi Arabia indicates that the incidence of postmenopausal osteoporosis (PMO) of 30% to 40% with over 60% having some degree of osteopenia (Mir Sadat-Ali, AbdulMohsen AlElq., Osteoporosis among male Saudi Arabs: a pilot study, Ann Saudi Med 2006; 26(6):450-454). In a prospective study of the prevalence of male osteoporosis among Saudi Arabs, the prevalence of osteoporosis among males was higher than Western males (Mir Sadat-Ali, AbdulMohsen AlElq., Osteoporosis among male Saudi Arabs: a pilot study, Ann Saudi Med 2006; 26(6):450-454). A study conducted in the central region of Saudi Arabia reported that healthy men have low bone mineral density, and the lumbar spine appears to be affected to a higher degree. Possible underlying causes include nutritional, life style and genetic factors (EL-DESOUKI Mahmoud; SULIMANI Riad A.; High prevalence of osteoporosis in Saudi men. Saudi medical journal, ISSN 0379-5284 2007, vol. 28, no. 5, pp. 774-777). More studies are needed to determine the national prevalence of male osteoporosis. It is recommended that serious measures to be undertaken to prevent male osteoporosis to stop any future epidemic of catastrophic osteoporosis-related fractures.

Osteoporosis has high prevalence in women; 1 in 3 women older than 50 years will eventually experience osteoporotic fractures, as will 1 in 5 men according to (International Osteoporosis Foundation, Facts and statistics about osteoporosis and its impact). Current Management of Fracture in osteoporosis is not different than that of standard fracture management in patients with normal bone density. It is thus mandatory to look at the fracture management of osteoporosis patients in a revolutionary manner owing to the poor and delayed healing of fractures in this wide spread disorder. Osteofragility fractures occur in men due to a compromise in bone strength, coupled with either trauma or a fall. In men at least 65 years of age, osteoporosis can be defined as bone mineral density (at the proximal femur, spine or distal forearm) of 2.5 standard deviations or less below the mean for a normal young adult man, using a male reference database (i.e., T-score value of $\leq -2.5$). In men 50-65 years of age, a similar definition is used if other risk factors for a fracture are present. Osteoporosis is increasingly recognized in men. One in three men aged >60 years will suffer an osteoporotic fracture. Spinal fractures occur in 5% of men (compared with 16% of women) and hip fractures in 6% of men (compared with 18% of women) >50 years of age. The risk of hip fracture increases by 2.6-fold for each standard deviation decrease in bone density measured at the hip. At present, the life expectancy for men has increased to a mean age of 76.8 years. With men now living longer, they can be expected to develop multiple coexisting illnesses contributing to bone loss and an increased likelihood of falling and fragility fractures. It is estimated that 30-60% of men presenting with spinal fractures have another illness contributing to their bone disease. The ideal therapy for men with osteoporosis should include an intervention which significantly increases bone strength and reduces fracture rates, is safe, easy to administer and economical.

SUMMARY OF THE INVENTION

The present invention provides a bone patch for bone regeneration, treatment of a fractured bone, and/or treatment of a bone disorder and/or a bone disorder, said bone patch comprising a composition of ingredients, said composition of ingredients comprising: stem cells; signaling molecules for osteoblast/endothelial differentiation; and scaffold material.

The present invention provides a method for treating a bone condition of an animal. The bone patch includes a composition of ingredients. The composition of ingredients include: stem cells; signaling molecules for osteoblast/endothelial differentiation; and scaffold material. The method for treating a bone condition includes: applying the bone patch to the animal for bone regeneration, treatment of a fractured bone, and/or treatment of a bone disorder.

DETAILED DESCRIPTION OF THE INVENTION

Figure 1:
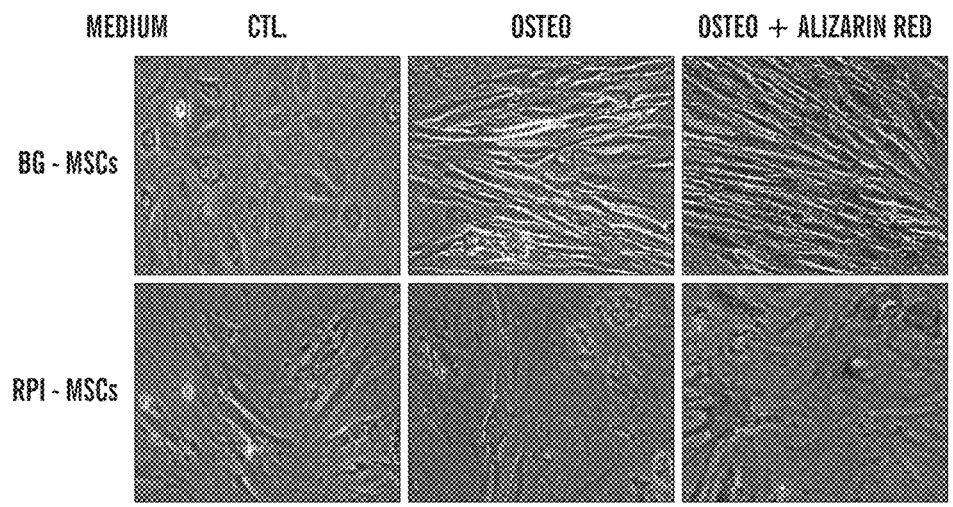
FIG. 1 depicts optimization of mesenchymal stem cell (MSC) differentiation towards endothelial cell progenitors, in accordance with embodiments of the present invention.

The present invention pertains to methods and compositions for bone patch to be applied to an animal (e.g., a human being or other species of animal) for treating a bone condition of the animal, such as for bone regeneration, treatment of fractured bones (e.g., as occurs in osteoporotic diseases), and/or treatment for bone disorders (e.g., osteoporosis).

The bone patches comprise stem cells (e.g., mesenchymal stem cell or other types of stem cells that differentiate into osteoblast and endothelial cells), signaling molecules for osteoblast/endothelial differentiation, and extracellular matrix scaffold in nanoformulations for optimal efficacy of the patch in a fracture healing microenvironment.

The bone patch comprises a composition of ingredients, said composition of ingredients comprising: stem cells; signaling molecules for osteoblast/endothelial differentiation; and scaffold material. The ingredients of the composition may be structured in a nanoformulation The developments of optimally effective and safe nanoformulations require a balanced inhibition of overactive osteoclast and stimulation of suppressed osteoblast in osteoporosis patients. In general the bone patch comprises stem cell, signaling molecules, and scaffold for optimal functionality and differentiation of stem cells into osteoblast for bone formation and into endothelial cells for neovascyulariztion and improved microenvironment.

Extracellular matrix (ECM) materials to be used in the fabrication of the scaffold. The scaffold promotes optimal efficacy of the patch in fracture healing. These scaffolds are synthetic ceramic type compounds, such as hydroxyapatite or other related materials. Efficiency of scaffolds could be controlled through pore size, biocompatibility, the 3-D nature of the scaffold, and load distribution. Some of the advantages to using a synthetic scaffold are ensured sterility, the use of a standardized product, and it can be customized. Some of the disadvantages are that it is difficult to mimic biologic scaffolds, they are expensive to manufacture, and they can have poor biocompatibility. The other option is to use, for the scaffold material, a biologic material such as collagen and/or fibrin as biological ECM. Some of the advantages to using biologic scaffolds are that they are inexpensive, biologically active, compatible with growth factors, and the pore size is helpful in vascular in-growth. Some of the disadvantages include a limited supply, cannot always ensure sterility, and they can be immunogenic. The process required to remove immunogenicity may decrease the physical properties of the scaffold. In addition, there is a need to ensure that there is an adequate blood and nutrient supply. Additionally, optimization of microenvironments and preconditioning of stem cell in vitro for optimal functionality in vivo will be accounted for through the control of oxygen, gases levels plus the ECM. The scaffold material is selected from the group consisting of collagen, fibrin, strontium, bone morphogenetic proteins (BMPs), hydroxyapatite, hyaluronan, hydrogel, poly(lactic-co-glycolic acid) (PLGA), chitosan, chitosan cross linked with fatty acid or bile acid, and combinations thereof.

Signaling molecules are used for stem cell proliferation and osteoblast/endothelial differentiation. Hence using PPARγ blockers as a signaling molecule might enhance the efficiency of MSC differentiation into osteoblast. Another genetic target is SIRT-1, which is an NAD-dependent histone deacetylase that plays a key role in chromatin remodeling. It has been found that calorie restriction upregulate SIRT-1 might play a key role in the reciprocal relationship between osteoblast and adipocyte differentiation from their common progenitor stem cell in the bone marrow, and this may possibly occur through action as a PPARγ repressor. SIRT-1 has been shown to increase osteoblastogenesis. Down-regulation of SIRT-1 inhibits osteoblastogenesis and increases adipogenesis. Flavonoids and isoflavones are effective up-regulators of SIRT-1 and might be useful signaling molecules for MSC differentiation to functional osteoblast. The signaling molecules are selected from the group consisting of estrogen-related compounds, calcitonin, oxytocin, parathyroid hormone (PTH), thyroid hormones, leptin, PPAR-γ suppressor, SIRT-1 inducers such as flavonoids and/or isoflavones, teriparatide, bone morphogenetic proteins (BMPs), cathepsin K inhibitors, melatonin, and combinations thereof.

Evidence supporting BMPs in bone fracture healing in the novel bone patches of the present invention is as follows. A randomized, controlled, single-blinded study was conducted in 450 patients with open tibia fractures. The control group received the current standard of care and the experimental group was treated with BMP in addition to the standard protocol. The results were measured based on the need for secondary intervention after the patients were treated. Some of the advantages of using BMP in these situations included: a 44% reduction in secondary intervention in the patients treated with BMP, faster fracture healing, fewer hardware failures, fewer infections, and faster wound healing. The main disadvantage of using BMP is that it is costly but in the bone patch very low levels are required since there are synergy with the other signaling molecules and ECM in the bone patch. Additionally, in spine surgery, fusions are performed to address deformity, instability and pain. BMP may be a beneficial therapeutic, such as: scoliosis, spondylolisthesis, osteomyelitis, discogenic pain associated with degenerative disc disease, and lumbar degenerative disc disease. Nine studies were conducted using BMP-2 (Infuse) and 3 studies were conducted using BMP-7 (OP-1). All of the studies used allograft bone as a control. Another randomized prospective study included 131 patients where 79 were treated with BMP-2 and 52 were in the ICBG control group. All patients received a follow-up exam in a minimum of 24 months. With a p value less than 0.001, there was a 96% increase observed in the fusion rate of the patients treated with BMP versus only a 71% fusion rate in the control group. The patients treated with BMP also endured a shorter average length of surgery, less blood loss, and a shorter hospital stay compared to the patients in the control group. According to the Oswestry Disability Index, patients treated with BMP showed improvement in the SF-36 physical component score and a low-back and leg pain score.

EXAMPLES

The role of stem cell in combination with nanoscaffold and humoral factors in assisting the healing of fractures in animal models, the said combination shall end in formulating therapeutic (Bone Patch). In this study new Zealand rabbit with induced osteoporosis and standard fracture will be used to in 2 groups, study and control. Each group is made of 20 rabbits to study the efficacy of the novel bone patch to be registered comprising or consisting of stem cell, growth factor and nanoscaffold in improving and shortening the healing period of the fractures in this osteoporotic animal model. The success in this model shall lead to better understanding of the healing process in osteoporosis and the possible assessment of the efficacy and safety in humans Example 1

The study is a prospective controlled trial on animal model using the New Zealand rabbit in which osteoporosis is induced. Following the diagnostic confirmation of osteoporosis the fracture is induced using a standard formula that induces an equivalent fracture in all animals. The animals are then divided into two groups (Group I and Group II) with 20 animals per group:

In Group I, healing of the fracture is allowed to progress with the aid of standard plaster cast and placebo.

In Group II, the standard plaster application is associated with the use of the novel bone patch.

Example 2

The bone patch comprises mesenchymal stem cells, nanoscaffold (hydroxyapatite), and signaling molecules.

For the cell preparation, a three kg New Zealand rabbit will be anesthetized by an intravenous injection of 5 ml of ketamine hydrochloride (Ketalar, Parke-Davis, Taiwan) and Rompum (Bayer, Leverkusen, Germany) mixture. Under sterile conditions, 10 ml of bone marrow aspi-rated from the iliac bone crest is collected into a syringe containing 6000 units of heparin to prevent clotting.

The marrow sample is washed with Dulbecco's phosphate buffered saline (DPBS) and disaggregated, by passing it gently through a 21-gauge intravenous catheter and syringe, to create a single cell suspension. Cells were recovered after centrifugation at 600 g for 10 minutes. Up to 2×10 8 nucleated cells in 5 ml of DPBS are loaded onto 25 ml of Percoll cushion Pharmacia Biotech, New Jersey, USA) of a density of 1.073 g/ml in a 50 ml conical tube. Cell separation is accomplished by centrifugation at 1100 g for 40 minutes at 20° C. The nucleated cells are collected from the interface, diluted with two volumes of DPBS and collected by centrifugation at 900 g. The cells are re-suspended, counted and plated at 2 10 cells/cm In T-75 flasks (Falcon Plastics, Bedford, Mass., USA).

The cells are maintained in Dulbecco's Modified Eagle's Medium-low glucose (DMEM-LG) (Gibco, Grand Island, N.Y., USA) containing 10% fetal bovine serum (FBS) and antibiotics (mixture of 100 units/ml of penicillin and 100 ug/ml of streptomycin) (Gibco, Grand Island, N.Y., USA) at 37° C. in a humidified atmosphere of 5% CO and 95% air. After 4 days of primary culture, the non-adherent cells are removed by changing the medium. The medium is changed every 3 days thereafter.

MSCs grow as symmetrical colonies and sub-cultured at 10 to 14 days. Subculture is carried out by treatment with 0.05% trypsin and 0.53 mM ethylenediaminetetraacetic acid (EDTA) for 5 minutes, rinsed from the substrate with serum-containing medium, collected by centrifugation at 800 g for 5 minutes and seeded into fresh flasks at 5000 to 6000 cells/cm2. Cultures are incubated at 37° C. in a humidified atmosphere of 5% CO and 95% air until cell confluence.

Regarding hydrogel and mesenchymal stem cells, Pluronic F127 purchased from Sigma Chemical Corporation (Sigma, St. Louis, Mo., USA). Pluronic F127 consists of approximately 70% ethylene oxide and 30% propylene oxide by weight. This material is soluble in water and enters a hydrogel state at room temperature. The Pluronic F127 powder is weighed and slowly added to the culture medium at a low temperature. The mixture is prepared at 20% (wt/vol) under the room temperature above 25° C. and sterilized by filtration through a 0.22 um pore-size Millipore filter. The culture medium is divided into two groups: group I being the control group (DMED-LG containing 10% FBS) and group II being the experiment group (osteogenic medium). MSCs suspension was mixed at 4 with a 30% solution of Pluronic F127 at a cellular concentration of 2 10 just before use. The mixture of MSCs and polymer was injected into a 24-well plate, at room temperature; this mixture of MSCs and polymer became gel-like. In group I, each well had DMED-LG containing 10% FBS added. In group II, each well had osteogenic medium added. In order to promote osteogenic differentiation, MSCs/hydrogel were cultured in an osteogenic medium (consisting of DMEM-LG containing 10% FBS, antibiotics, 100 uM ascorbate-2-phosphate, 10 M dexamethasone and 10 mM glycerophosphate).

Example 3

The osteogenic potential of MSCs/hydrogel is evaluated. To determine the osteogenic differentiation potential of MSCs in hydrogel, four tests are performed on the cultures on day 7 and 14: Alizarin Red S staining, reverse transcription polymerase chain reaction (RT-PCR), alkaline phosphatase (ALP) activity measurements and calcium quantification.

Alizarin Red S staining is performed. Alizarin Red staining is used for detecting calcium deposits. For osteogenesis studies, MSCs are cultured for 14 days with a composite made of Pluronic F127 and Interpore. The medium is then replaced with a calcification medium consisting of complete medium supplemented with 10M dexamethasone, 20 mM ?-glycerol phosphate and 50 ug/ml ascorbate-2-phosphate for an additional 7 and 14 days. These cultures in dishes are stained with 0.5% Alizarin Red solution. Sections stained with Alizarin Red were then examined under a polarized light microscope.

The progress of fracture induced by APD (3-amino-1-hydroxypropylidene-1,1-bisphosphonate), a drug known to block osteoclast activity to assist in clinical usage of these drugs. 20 four-month-old female New Zealand white rabbits are administered APD induced by intra-articular injection of carrageenan into the right tibiofemoral joint, at the dosage of 0.3 Mg/kg/day. The experiment lasted 7 weeks (Bellingham C M, Lee J M, Moran E L, Bogoch E R., Bisphosphonate (pamidronate/APD) prevents arthritis-induced loss of fracture toughness in the rabbit femoral diaphysis, J Orthop Res. 1995; 13(6):876-80).

The healing of fracture is monitored. The following are the performance indicators for efficacy and safety of the bone patch in both groups: (i) the healing is monitored in both groups using duration of healing; (ii) radiological and biochemical changes to assess the fracture healing; (iii) the improvement in osteoporosis bone densitometry, (iv) bone turnover parameters during and after healing with serial measurement, and (v) safety of bone patch and any arising side effects.

In the method of the present invention, the cathepsin inhibitors may be administered alone or in conjunction with chemotherapeutic agents. They may be administered by the same or different route of administration as the chemotherapeutic agents. Further, the cathepsin inhibitor may be administered before, during, or after administration of a chemotherapeutic agent. More than one cathepsin inhibitor may be administered at once, or in successive administrations. More than one chemotherapeutic agent may also be administered with a cathepsin inhibitor.

A composition of the present invention may be administered in any desired and effective manner: as compositions for local implant at the site of fractured bone, or for parenteral or other administration in any appropriate manner such as intraperitoneal, subcutaneous, topical or intramuscular, and combinations thereof.

Regardless of the route of administration selected, the composition of the bone patch may be formulated into pharmaceutically-acceptable dosage forms by conventional methods known to those of ordinary skill in the art (e.g., see: *Remington's Pharmaceutical Sciences*, Mack Publishing Co., Easton, Pa.). Pharmaceutical carriers are well known in the art (e.g., see: *Remington's Pharmaceutical Sciences cited above and The National Formulary*, American Pharmaceutical Association, Washington, D.C.) and include sugars (e.g., lactose, sucrose, mannitol, and sorbitol), starches, cellulose preparations, calcium phosphates (e.g., dicalcium phosphate, tricalcium phosphate and calcium hydrogenphosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly[orthoesters], and poly[anhydrides]), elastomeric matrices, liposomes, microspheres, oils (e.g., corn, germ, olive, castor, sesame, cottonseed, and groundnut), cocoa butter, waxes, paraffins, silicones, talc, silicylate, and the like. Suitable carriers used included in the composition of the present invention should be compatible with the other ingredients of the composition. Carriers suitable for a selected dosage form and intended route of administration are well known in the art, and acceptable carriers for a chosen composition, dosage form and method of administration can be determined using ordinary skill in the art.

The composition of the present invention may, optionally, contain one or more additional agents which include but are not limited to: (1) fillers or extenders, such as starches, lactose, sucrose, glucose, mannitol, silicic acid or the like; (2) binders, such as carboxymethylcellulose, alginates, gelatin, polyvinyl pyrrolidone, hydroxypropylmethyl cellulose, sucrose, acacia or the like; (3) humectants, such as glycerol or the like; (4) disintegrating agents, such as agar-agar, calcium carbonate, potato or tapioca starch, alginic acid, certain silicates, sodium starch glycolate, cross-linked sodium carboxymethyl cellulose, sodium carbonate or the like; (5) solution retarding agents, such as paraffin or the like; (6) absorption accelerators, such as quaternary ammonium compounds or the like; (7) wetting agents, such as acetyl alcohol, glycerol monostearate or the like; (8) absorbents, such as kaolin, bentonite clay or the like; (9) lubricants, such as talc, calcium stearate, magnesium stearate, solid polyethylene glycols, sodium lauryl sulfate or the like; (10) suspending agents, such as ethoxylated isostearyl alcohols, polyoxyethylene sorbitol and sorbitan esters, microcrystalline cellulose, aluminum metahydroxide, bentonite, agar-agar, tragacanth or the like; (11) buffering agents; (12), excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, polyamide powder or the like; (13) inert diluents, such as water, other solvents or the like; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, waxes or the like; (18) opacifying agents; (19) adjuvants; (20) emulsifying and suspending agents; (21), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols, fatty acid esters of sorbitan or the like; (22) propellants, such as chlorofluorohydrocarbons or the like and volatile unsubstituted hydrocarbons, such as butane, propane or the like; (23) antioxidants; (24) agents which render the formulation isotonic with the blood of the intended recipient, such as sugars, sodium chloride or the like; (25) thickening agents; (26) coating materials, such as lecithin or the like; and (27) sweetening, flavoring, coloring, perfuming and preservative agents. Each such ingredient or material should be compatible with the other ingredients of the formulation. Agents suitable for a selected dosage form and intended route of administration are well known in the art, and acceptable ingredients and materials, dosage form and method of administration may be readily determined by those of ordinary skill in the art.

A composition in accordance with the present invention that is suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste.

FIG. 1 depicts optimization of mesenchymal stem cell (MSC) differentiation towards endothelial cell progenitors, in accordance with embodiments of the present invention. With the present invention, the mesenchymal stem cells can differentiate toward osteoblasts.

Figure 2:
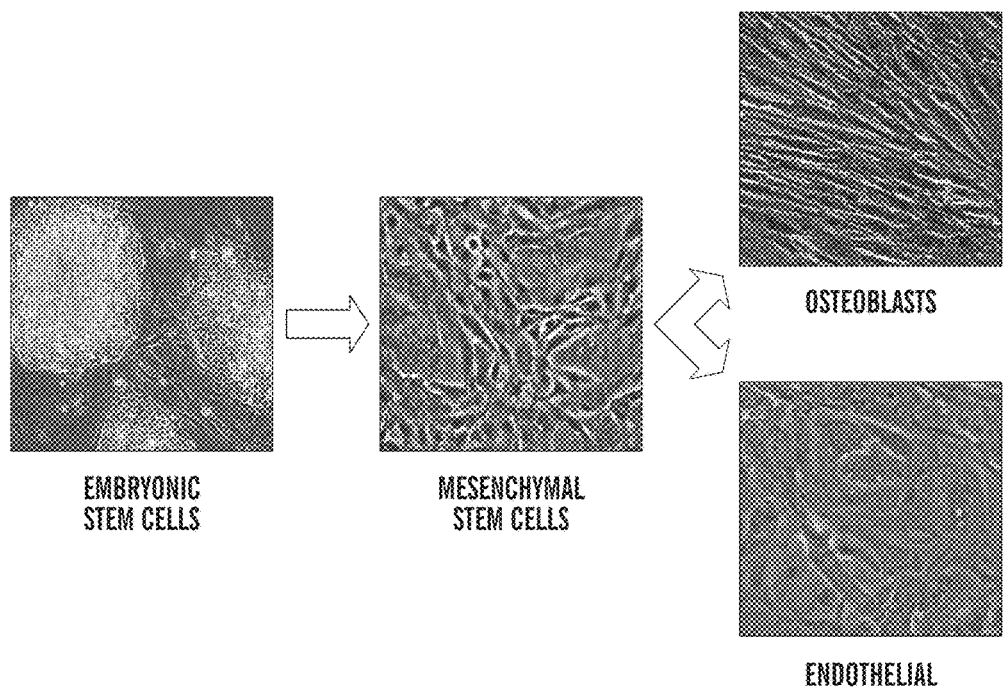
FIG. 2 depicts mesenchymal stem cell entry into osteoplasts and endothelial cells, in accordance with embodiments of the present invention.

FIG. 2 depicts mesenchymal stem cell entry into osteoplasts and endothelial cells, in accordance with embodiments of the present invention While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A method for treating a bone condition of an animal, said method comprising:
applying a bone patch to a location on the animal at which the bone patch is effective for treating the bone condition, said bone patch comprising a composition of ingredients, said composition of ingredients comprising:

scaffold material comprising synthetic ceramic material;

mesenchymal stem cells added to the scaffold material; and signaling molecules for differentiation of the mesenchymal stem cells into osteoblast cells and endothelial cells, wherein the signaling molecules comprise oxytocin, leptin, PPAR-γ suppressor, SIRT-1 inducers, and cathepsin K inhibitors.

2. The method of claim 1, wherein the animal is a human being.

3. The method of claim 1, wherein the animal is a non-human species of animal.

4. The method of claim 1, wherein the bone condition being treated is osteoporosis.

5. The method of claim 1, wherein the bone condition being treated is a fractured bone.

6. The method of claim 1, wherein said treating the bone condition results in bone regeneration in the animal.

7. The method of claim 1, wherein the composition of the bone patch is in a pharmaceutically-acceptable dosage form.

* * * * *